United States Patent
Pavani

(10) Patent No.: US 9,523,645 B2
(45) Date of Patent: Dec. 20, 2016

(54) LENTICULAR WAFER INSPECTION

(71) Applicant: Sri Rama Prasanna Pavani, Palo Alto, CA (US)

(72) Inventor: Sri Rama Prasanna Pavani, Palo Alto, CA (US)

(73) Assignee: Exnodes Inc., Palo Alto, CA (US)

( * ) Notice: Subject to any disclaimer, the term of this patent is extended or adjusted under 35 U.S.C. 154(b) by 248 days.

(21) Appl. No.: 14/519,054

(22) Filed: Oct. 20, 2014

(65) Prior Publication Data

US 2016/0109376 A1 Apr. 21, 2016

(51) Int. Cl.
*G01N 21/88* (2006.01)
*G01N 21/95* (2006.01)
*G01B 11/26* (2006.01)
*G03F 9/00* (2006.01)

(52) U.S. Cl.
CPC .......... *G01N 21/8806* (2013.01); *G01B 11/26* (2013.01); *G01N 21/9501* (2013.01); *G03F 9/7088* (2013.01); *G01N 2021/8822* (2013.01); *G01N 2201/06113* (2013.01); *G01N 2201/12* (2013.01)

(58) Field of Classification Search
CPC ................................ G01B 11/26; G03F 9/7088
See application file for complete search history.

(56) References Cited

U.S. PATENT DOCUMENTS

| | | | |
|---|---|---|---|
| 6,133,986 A * | 10/2000 | Johnson | G02B 21/0028 355/43 |
| 6,628,390 B1 | 9/2003 | Johnson | |
| 6,878,937 B1 * | 4/2005 | Mankos | G01N 23/203 250/306 |
| 7,180,586 B2 | 2/2007 | Neumann et al. | |
| 7,477,403 B2 * | 1/2009 | Gui | G03F 7/70275 355/77 |
| 7,724,362 B1 | 5/2010 | Rosengaus | |
| 9,086,536 B2 * | 7/2015 | Pang | G02B 5/1842 |
| 2014/0296719 A1 * | 10/2014 | Sato | A61B 5/1455 600/476 |
| 2015/0002835 A1 * | 1/2015 | Kuo | G01N 21/9501 356/72 |

FOREIGN PATENT DOCUMENTS

JP  60113937 A * 6/1985

* cited by examiner

*Primary Examiner* — Charlie Y Peng

(57) ABSTRACT

A system and method for inspecting a surface, comprising: illuminating said surface with an electromagnetic radiation to generate scattered radiation from features of said surface; inducing a change in phase to said scattered radiation for reducing divergence of said scattered radiation and for redirecting said scattered radiation towards a predetermined spatial region; focusing after said radiation has propagated to said spatial region; capturing an image of radiation, whereby said features of said surface are detected in said image of radiation.

20 Claims, 7 Drawing Sheets

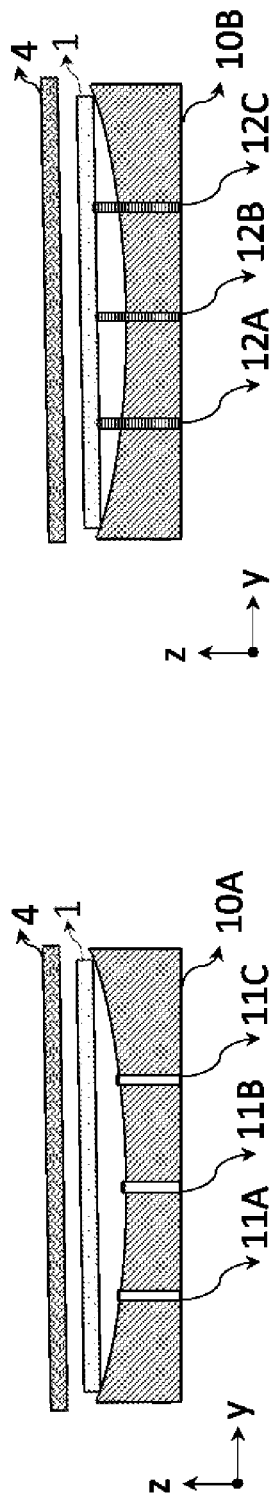
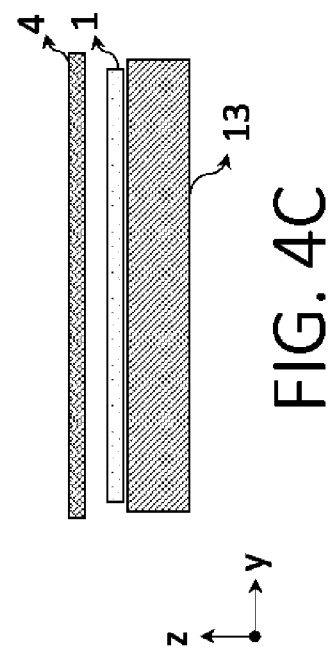

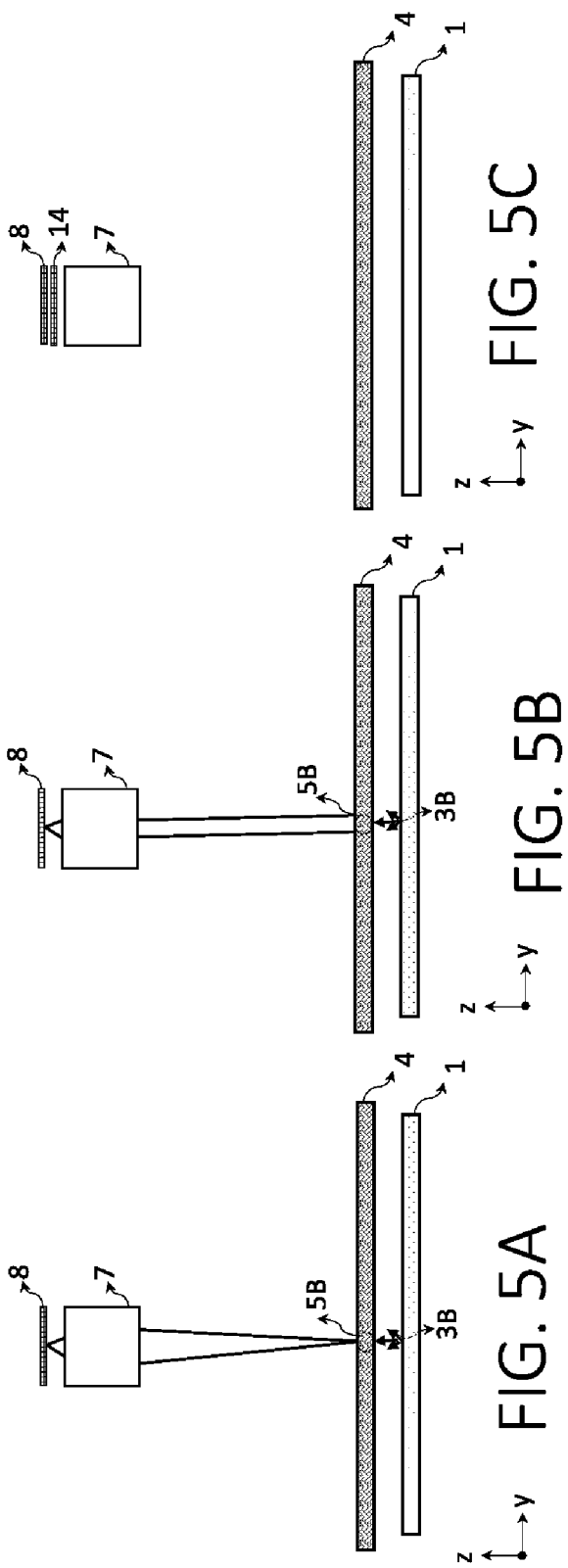

LENTICULAR WAFER INSPECTION

FIELD OF THE INVENTION

This invention relates generally to wafer inspection and more particularly to lenticular wafer inspection having a wide field of view and a large numerical aperture.

BACKGROUND

Yield is a key performance metric in the fabrication of semiconductor integrated circuit (IC) components used in modern electronic devices. ICs have intricate nanometer scale structures to perform high speed processing. These nanometer scale structures need be fabricated precisely. A deviation from tolerable limits of excursion during fabrication could cause anything between performance degradation to a complete failure of ICs. Fabrication of ICs involve hundreds of steps that span a several weeks. Yield is defined as the ratio of number of ICs that meet performance targets to the total number of manufactured ICs. An important goal in semiconductor fabrication is to maximize yield. To maximize yield, it crucial to identify and eliminate root causes of problems that affect yield. Measuring yield numbers at the end of IC fabrication, although necessary, is often not sufficient for identifying root causes of problems because of the extensive number and the complexity of steps involved in semiconductor fabrication. In order to identify root causes more effectively, semiconductor wafers are inspected for abnormalities or defects throughout the fabrication process, often after each significant process step. By inspecting for yield-affecting defects at a number check points, root causes of problems could be more readily identified and eliminated.

Dark-field wafer inspection is a widely used traditional method for detecting defects on wafers. In a dark-field wafer inspection tool, a laser beam is incident on the surface of a wafer to illuminate a tiny spot. Most of the laser beam undergoes specular reflection because semiconductor wafers are very smooth. An infinitesimally small amount of light—a few photons out of a million incident photons—is scattered when a defect is present in the region of wafer illuminated by the spot. A collection optic with a large numerical aperture collects scattered radiation and focuses the radiation on a detector. The electrical signal from the detector is analyzed to determine the presence of a defect in the region of wafer under the tiny spot. In order to inspect the entire surface area of the wafer, the wafer is scanned relative to the spot sequentially. Since the size of the spot is very small in comparison to the area of wafer surface, about a billion different points of the wafer are often sequentially scanned to inspect the entire surface of the wafer. While such scanning is an inherently slow process, efforts are often made to speed up scanning by moving the surface of the wafer at a very high speed.

With every new generation of semiconductor fabrication technology, the size of IC components have been becoming smaller. The reducing size of IC components also reduces the size of defects that affect yield. This is because the structures in ICs are sensitive to defects whose sizes are at least as big as the structures. Consequently, wafer inspection tools are expected to improve their defect sensitivity performance at the same rate as the shrinking of IC structures. Unfortunately, wafer inspection tools have not been keeping up. In the last ten years, while the smallest IC structures shrank from 130 nm to 14 nm (over 9× reduction), defect sensitivity improved from 50 nm to 20 nm (2.5× reduction). As a result, yield of modern ICs have been suffering.

In addition to demanding improved defect sensitivity, semiconductor fabrication also requires wafer inspection tools to have a high inspection throughput. Throughput refers to the number of wafers inspected per hour. In other words, semiconductor fabs desire to achieve maximum defect sensitivity by spending minimum amount of time for inspecting a wafer. Unfortunately, in traditional wafer inspection tools, sensitivity and throughput are opposing entities that exhibit a trade-off. In these tools, an increase in sensitivity decreases throughput, and an increase in throughput decreases sensitivity. This is because a throughput increase in traditional tools increases scanning speed; reduces scanning time per wafer; decreases scattered light energy; and decreases defect sensitivity.

The requirement to scan a tiny spot on a large wafer area originates because of the small field of view of a traditional wafer inspection system. The small field of view constraint is primarily a practical consequence of having a collection optic with a large numerical aperture required to capture radiation scattered in a wide range of polar and azimuthal angles.

A number of drawbacks are present in traditional wafer inspection tools, including: a) reduced throughput; b) reduced sensitivity; c) trade-off between sensitivity and throughput; d) complex high-speed scanning requirement; e) trade-off between field of view and numerical aperture; f) wafer deformation due to high-speed scanning; and g) reduced reliability due to components moving at high speeds.

Accordingly, there is a need for an improved wafer inspection system that can increase throughput; increase sensitivity; relax dependence of sensitivity on throughput; relax high-speed scanning requirement; relax the trade-off between field of view and numerical aperture; minimize wafer deformation; and increase reliability.

SUMMARY

The invention is a system and method for lenticular wafer inspection having a wide field of view and a large numerical aperture.

In some embodiments, the invention is a system for inspecting a surface, comprising: an electromagnetic radiation incident on said surface to generate scattered radiation from features of said surface; a micro-optic layer disposed to induce a change in phase for reducing divergence of said scattered radiation and for redirecting said scattered radiation towards a predetermined spatial region; an imaging optic located in said spatial region to focus said radiation from said micro-optic layer; and an image sensor positioned to detect radiation from imaging optic to generate an image of radiation, whereby said features of said surface are detected in said image of radiation.

In some embodiments, the invention is a method for inspecting a surface, comprising: illuminating said surface with an electromagnetic radiation to generate scattered radiation from features of said surface; inducing a change in phase to said scattered radiation for reducing divergence of said scattered radiation and for redirecting said scattered radiation towards a predetermined spatial region; focusing after said radiation has propagated to said spatial region; capturing an image of radiation, whereby said features of said surface are detected in said image of radiation.

BRIEF DESCRIPTION OF THE DRAWINGS

FIG. 4A illustrates a cross-section showing the use of a gas vent for holding a surface flat, in accordance with the invention.

FIG. 4B illustrates a cross-section showing the use of supporting structures that make contact with a surface to hold a surface flat, in accordance with the invention.

FIG. 4C illustrates a cross-section showing a flat surface, in accordance with the invention.

FIG. 5A depicts a cross-section of a lenticular wafer inspection system with an imaging optic focusing an image of micro-optic layer on image sensor, in accordance with the invention.

FIG. 5B depicts a cross-section of a lenticular wafer inspection system with an imaging optic focusing an image of surface on image sensor, in accordance with the invention.

FIG. 5C depicts a cross-section of a lenticular wafer inspection system with an image sensor comprising a micro-optic sensor layer, in accordance with the invention.

DETAILED DESCRIPTION OF THE PREFERRED EMBODIMENTS

Figure 1:
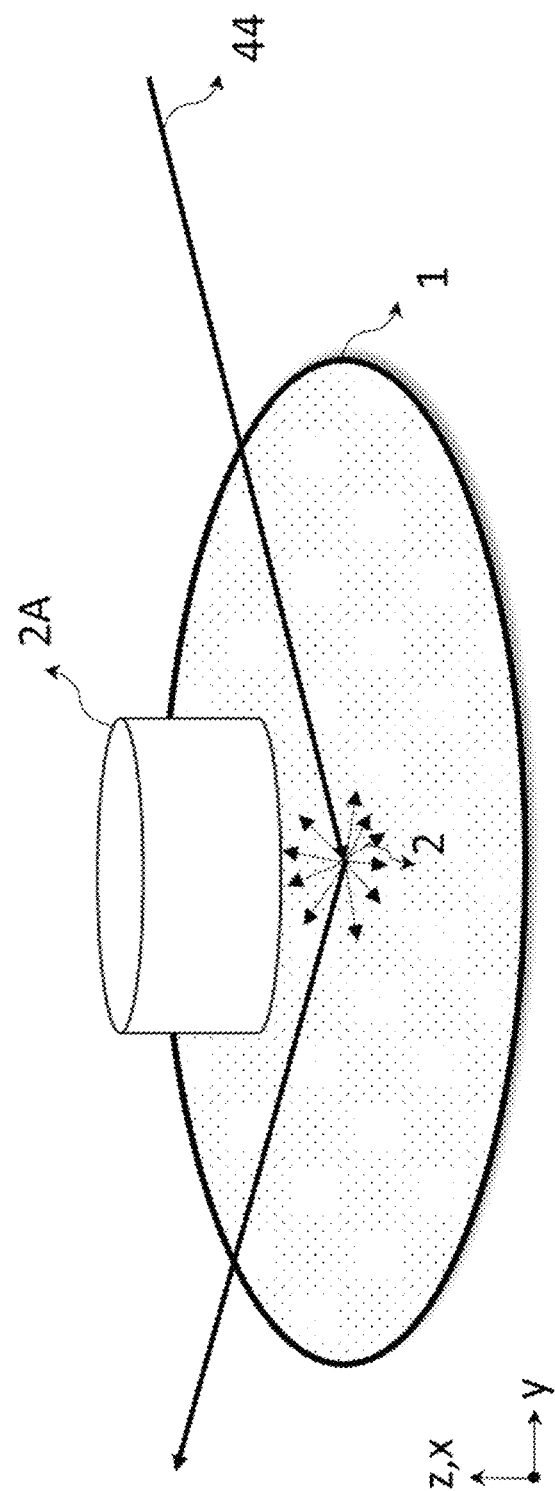
FIG. 1 shows a traditional wafer inspection system, according to prior art.

FIG. 1 shows a traditional wafer inspection system, according to prior art. A laser beam 44 is incident on a surface 1 to illuminate a spot. Surface 1 is mostly flat and smooth, so a majority of incident photons undergo specular reflection. Occasionally, an abnormality or defect that deviates from the flat and smooth nature of surface 1 is present under the illumination spot. The defect scatters a portion of incident illumination. The amount of power in scattered light 2 is dependent on the properties of the defect (such as its size and material composition), incident illumination (such as intensity, wavelength, polarization, and angle of incidence), and properties of surface 1 (such as its refractive index). In modern semiconductor fabrication, the size of defects can be as small as a few tens of nanometers. Typical scattered power from defects is an infinitesimally small fraction of the power in incident illumination. For example, some defects scatter not more than a few photons out of a million incident photons. The scattered light is collected with a collection optic 2A having a large numerical aperture. A large numerical aperture helps in collecting light scattered in a wide range of polar and azimuthal angles. The collection aperture has a small field of view that approximately matches the dimension of the illuminated spot. The collected light is focused on a photodetector to generate an electrical output.

The field of view of the system in FIG. 1 is extremely small in comparison to the surface area of surface 1. Spot sizes are typically in tens of microns and surface diameters can be as large as 450 millimeters. This could require the spot to illuminate as many as a billion different points to scan the entire area of surface 1. Since scanning such a large number of spots is a time taking process, surface 1 is moved at a very high speed to improve throughput. However, any improvement in throughput comes at the price of defect sensitivity. The faster the speed of scanning, the smaller the amount of time the spot spends on a defect. Therefore, higher throughput reduces the energy of scattered radiation, and consequently reduces defect sensitivity.

The electrical output of photodetector typically comprises of three components: a) signal from light scattered by defect, b) background from light scattered by surface roughness (haze), and c) detector noise. The three components are mixed with each other. By comparing the electrical output from different points on wafer, excursions of signal from an otherwise uniform background can be determined as being caused by the presence of a defect.

The traditional wafer inspection system of FIG. 1 suffers from a number of drawbacks, including: a) reduced throughput due to extensive scanning requirement; b) reduced sensitivity to defect properties, such as shape, due to a limited number of photodetectors; c) trade-off between sensitivity and throughput because of the dependence of total scattered light energy on the amount of time a defect is illuminated; d) complex high-speed scanning requirement due to the need to maximize throughput of an inherently slow scanning system; e) trade-off between field of view and numerical aperture, because of increased off-axis aberrations in collection optics having a large numerical aperture; f) wafer deformation due to air currents created by high-speed scanning of wafer; and g) reduced reliability due to high-speed moving parts needed to achieve an improvement in throughput.

Figure 2:
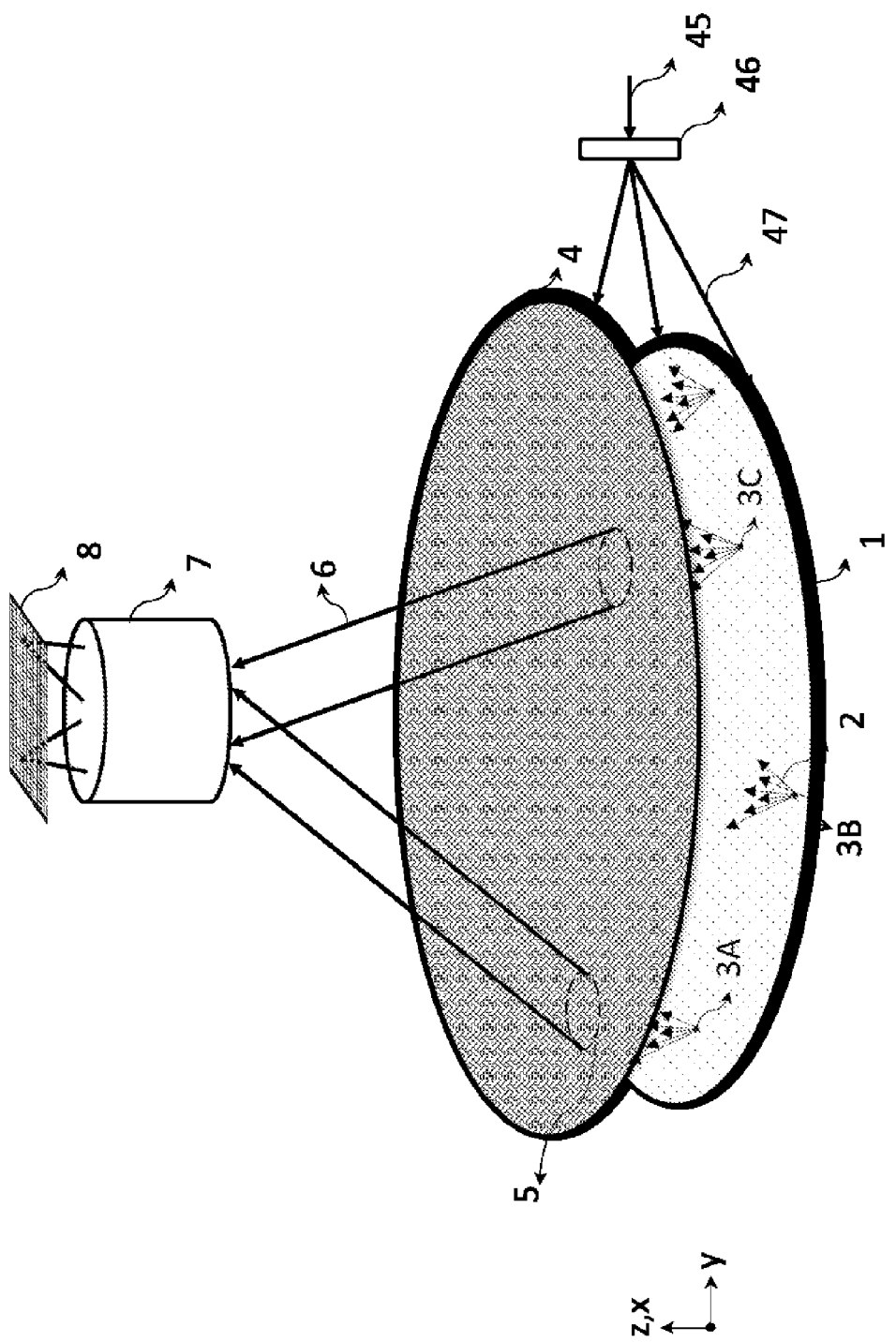
FIG. 2 illustrates a lenticular wafer inspection system with a micro-optic layer, in accordance with the invention.

FIG. 2 illustrates a lenticular wafer inspection system with a micro-optic layer 4, in accordance with the invention. An electromagnetic beam 45 is incident on a beam expander 46 to generate an expanded beam 47. The expanded beam 47 illuminates a surface 1. Defects 3A, 3B, and 3C present on surface 1 generate scattered radiation. Since surface 1 is mostly smooth, a majority of the incident electromagnetic beam undergoes specular reflection. The scattered radiation 2 diverges upon propagation. The diverging scattered radiation is incident on a micro-optic layer 4. The micro-optic layer reduces the divergence of scattered radiation and redirects the radiation towards an imaging optic 7. In some embodiments, micro-optic layer 4 collimates the scattered radiation. By reducing the divergence of scattered radiation, the micro-optic layer keeps the scattered radiation from expanding any further. In doing so, the micro-optic layer makes it sufficient for the imaging optic 7 to have a small aperture that is just large enough to collect the scattered radiation 6 having a reduced divergence. The imaging optic 7 is designed to have a field of view that is wide enough to image the entire area of surface 1 and micro-optic array 4. In addition to reducing the divergence of scattered radiation, the micro-optic layer also redirects scattered radiation towards the imaging optic. The angle by which the scattered radiation needs to be redirected depends on the location of the defect generating the scattered radiation. The farther the defect lies from the point of intersection of optical axis of imaging optic and micro-optic layer, the larger the angle of redirection. For example, a defect lying close to the optical axis of imaging optic is redirected by an angle that is smaller than the redirection angle for a defect lying farther from the optical axis of imaging optic 7. The imaging optic collects radiation with reduced divergence from the entire area of the micro-optic layer and focuses the radiation on an image sensor 8. The image sensor 8 may be of a complementary metal oxide semiconductor (CMOS) or a charge coupled device (CCD) type. A number of photodetectors, called pixels, are arranged as a two dimensional matrix in the image sensor. In some embodiments, the imaging optic 7 is focused to form an image of the micro-optic layer 4 on the image sensor. In other embodiments, the imaging optic 7 is focused to form an image of surface 1 on the image sensor. The micro-optic array comprises of a number of micro-apertures 5, each having its own optical axis passing through the center of the micro-apertures. In some embodiments, the micro-optic layer is designed to redirect scattered radiation originating from defects that lie in the region where the optical axis of micro-aperture intersects surface 1. In some embodiments, the surface may be scanned to a allow a plurality of points on the surface to fall within the region around the optical axis of micro apertures. Since there are numerous micro-apertures present on the micro-optic layer 4, the area of scanning required is very small in comparison to the entire area of surface 1. The scanning area reduces as the number of micro-apertures are increased. For example, if the micro-optic array comprises 1000 micro-apertures, then the area to be scanned is 0.1% of the area of surface 1. When the number of micro-apertures is increased to 10000, then the area to be scanned reduces to only 0.01% of the area of surface 1.

In some embodiments, the wavelength of electromagnetic beam 45 is designed to maximize reflected power from surface 1. The reflection coefficient of surface 1 is dependent on the refractive index of surface 1, and the refractive index of surface 1 exhibits a dependence on wavelength of beam 45. Therefore, the wavelength of the electromagnetic beam 45 can be designed to maximize refractive index, and consequently maximize reflected power. Reflected power coefficient is calculated as the square of reflection coefficient. In some embodiments, the wavelength of beam 45 is designed to maximize the difference in refractive index between surface 1 and the medium in which beam 45 propagates immediately before illuminating surface 1. Maximizing this difference in refractive index increases reflected power and scattered intensity from defects. The intensity of scattered light from a defect is inversely proportional to the fourth power of wavelength. Lower wavelengths are therefore more desirable to maximize the intensity scattered radiation. In some embodiments, the wavelength of electromagnetic radiation is chosen as the smallest wavelength that maximizes the refractive index of surface 1. In other embodiments, the wavelength of electromagnetic radiation is chosen as the wavelength at which the intensity of scattered radiation from a defect located on surface 1 is maximized. In some embodiments, electromagnetic beam 45 has a wavelength that maximizes quantum efficiency of image sensor 8. Quantum efficiency of a photodetector is the ratio of the number of photoelectrons detected by the photodetector to the number of photons incident on the photodetector. Quantum efficiency of a detector exhibits a dependence on wavelength of electromagnetic radiation incident on it. The sensitivity of the photodetector, defined as the smallest detectable number of photons, and the signal to noise ratio of the photodetector can be maximized by choosing a wavelength that maximizes the quantum efficiency of the photodetectors. Maximizing the quantum efficiency of photodetectors present in image sensor 8 improves the quality of images detected by image sensor 8. In some embodiments, the polarization of electromagnetic beam 45 is designed to maximize reflected power from surface 1. In some embodiments, an s-polarization (perpendicular to the plane of incidence) is used for beam 45 to maximize reflected power from surface 1. S-polarized radiation also maximizes scattered light from defects. In some embodiments, the angle of incidence of electromagnetic beam 45 is designed to maximize reflected power from surface 1. Angle of incidence refers to the angle beam 45 makes with the normal of surface 1. The reflection coefficient of surface 1 increases as the angle of incidence of a beam increases.

Figure 3:
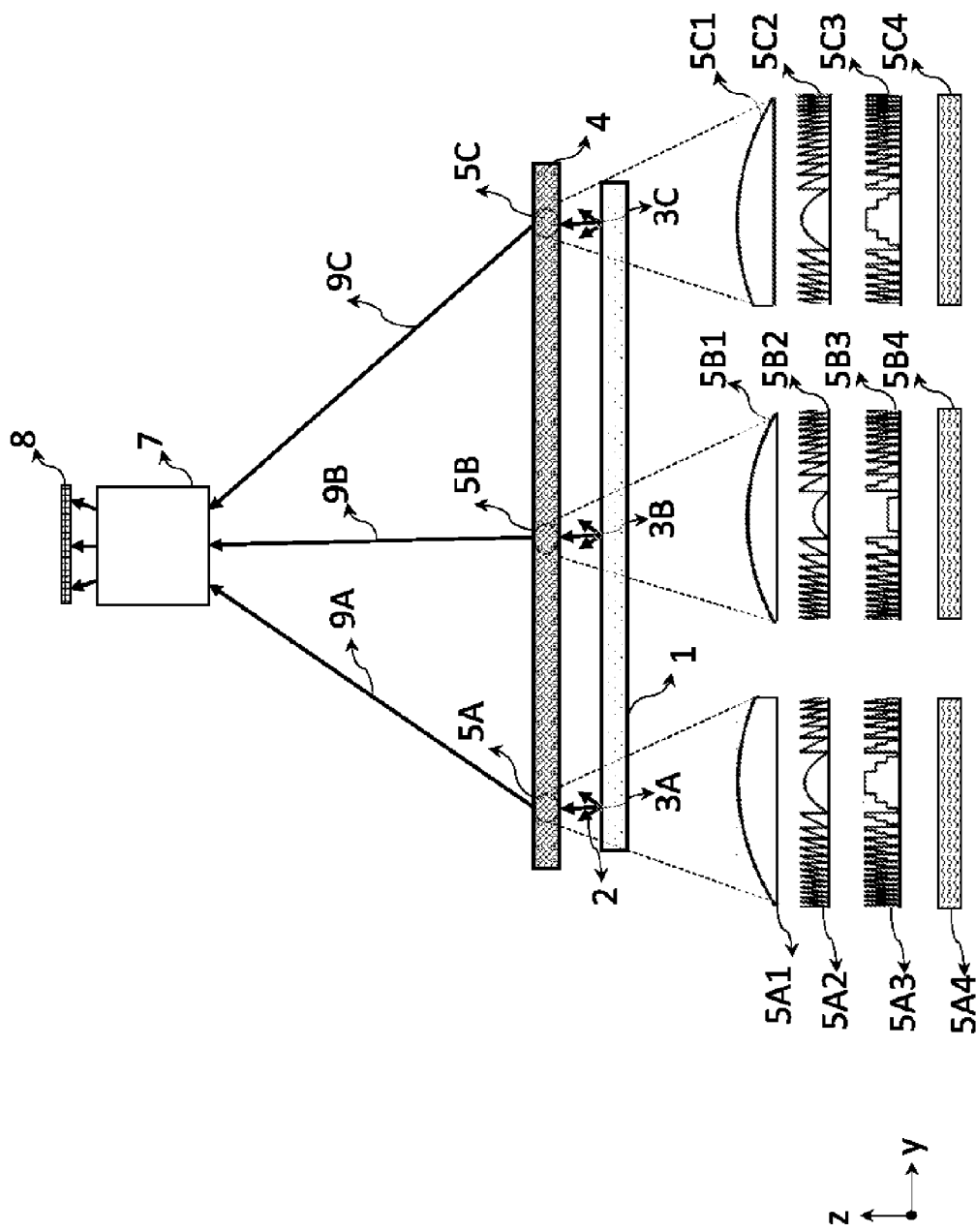
FIG. 3 depicts a cross-section of a lenticular wafer inspection system with a micro-optic layer comprising a refractive, diffractive, quantized diffractive, or a gradient index element, in accordance with the invention.

FIG. 3 depicts a cross-section of a lenticular wafer inspection system with a micro-optic layer 4 comprising a refractive, diffractive, quantized diffractive, or a gradient index element, in accordance with the invention. The cross-section shows a surface 1 having three defects, 3A, 3B, and 3C, which generate scattered radiation. The scattered radiation 2 diverges and is incident on a micro-optic layer 4. The micro-optic layer reduces the divergence of the scattered radiation and redirects the scattered radiation towards an imaging optic 7. The scattered radiation with reduced divergence, 9A, 9B, and 9C, are focused by imaging optic 7 on to an image sensor 8. The micro-optic layer 4 comprises a number of micro-apertures for reducing the divergence of scattered radiation and for redirecting the scattered radiation. The scattered radiation from defect 3A is incident on a micro-aperture 5A present in the micro-optic layer 4. Similarly, scattered radiations from defects 3B and 3C are incident on micro-apertures 5B and 5C, respectively. A refractive optical implementation of micro-aperture 5A comprises of a combination of a convex lens and a prism. In some embodiments, the prism is designed as a linear phase element. This combination, called linear phase lens 5A1, reduces the divergence of scattered radiation originating from defect 3A and redirects the scattered radiation towards imaging optic 7. The focal length of the linear phase lens is substantially equal to the distance between the micro-aperture 5A and defect 3A. Since the defect is present near the focal point of the linear phase lens, the scattered radiation from the defect is approximately collimated by the lens. In other words, the divergence of the scattered radiation is reduced close to zero by the linear phase lens. By doing so, the width of scattered radiation 9A substantially remains the same as it propagates from the micro-optic layer 4 to imaging optic 7. The linear phase element component of the linear phase lens 5A1 redirects scattered radiation towards imaging optic 7. In the absence of this linear phase component, scattered radiation 9A would propagate in a direction orthogonal to the micro-optic array, thereby missing imaging optic 7. Having the linear phase element ensures that scattered radiation 1 from defect 3A reaches imaging optic 7. In some embodiments, the phase gradient of linear phase element is proportional to the distance between said element and the point of intersection of the optical axis of imaging optic 7 with a micro-optic layer comprising an array of prisms. The azimuthal direction of the linear phase element is substantially equal to the direction of the above mentioned point of intersection from the linear phase element. In some embodiments, the linear phase element is combined with the convex lens as a summation to design a linear phase lens. $LPL(x,y) = \alpha(x^2+y^2) + \beta x + \gamma y$, where $LPL(x,y)$ refers to the thickness or sag of a linear phase lens, $\alpha$ is the coefficient of quadratic phase component, $\beta$ is the coefficient of linear phase component along x dimension, and $\gamma$ is the coefficient of linear phase component along y dimension. The phase retardation seen by scattered radiation 2 due to $LPL(x,y)$ can be expressed as $e^{(ik\ LPL(x,y))}$, were $k=2\pi n/\lambda$, $\lambda$ is the wavelength of scattered radiation, and n is refractive index of the medium of the linear phase lens. The quadratic phase component of $LPL(x,y)$ implements the convex lens to reduce the divergence of scattered radiation, and the linear phase components of $LPL(x,y)$ implement the linear phase element to redirect scattered radiation 2 to reach imaging optic 7. The focal length of the convex lens is dependent on the quadratic phase coefficient α. The focal length can be increased by decreasing α. Alternatively, the focal length can be decreased by increasing α. The redirection of scattered radiation along the x dimension can be controlled by the linear phase coefficient β. The redirection angle along x dimension can be increased by increasing β, and can be decreased by decreasing β. The redirection of scattered radiation along the y dimension can be controlled by the linear phase coefficient γ. The redirection angle along y dimension can be increased by increasing γ, and can be decreased by decreasing γ. The refractive optical implementations, linear phase lenses, of micro-apertures 5B and 5C are shown in 5B1 and 5C1. In some embodiments, the quadratic phase coefficients of linear phase lenses, 5A1, 5B1, and 5C1, are similar. Accordingly, they have similar focal lengths. The rationale behind having similar focal lengths is that the distance between micro-aperture 5A and defect 3A is the similar to the distance between micro-aperture 5B and defect 3B. Further, the distance between micro-aperture 5C and defect 3C is also the similar to the distance between micro-aperture 5B and defect 3B. In some embodiments, micro-optic layer 4 is aligned parallel to surface 1. The linear phase components of linear phase lenses, 5A1, 5B1, and 5C1, are all different from each other. Defect 3B lies on the optical axis on imaging optic 7, and the center of micro-aperture 5B coincides with the optical axis of imaging optic 7. Therefore, scattered radiation from micro-aperture 5B is already in perfect alignment to reach imaging optic 7 without any redirection. Accordingly, the linear phase coefficient γ is zero in linear phase lens 5B1. However, this is not the case for micro-apertures 5A and 5B. The optical axis of imaging optic 7 does not coincide with the centers of micro-apertures 5A and 5B. Accordingly, scattered radiation from micro-apertures 5A and 5B need to be redirected towards imaging optic 7. The linear phase coefficient γ has a non-zero positive value in linear phase lens 5A1. Accordingly, micro-aperture 5A redirects scattered radiation 2 to the right side of its optical axis so as to direct radiation from defect 3A towards imaging optic 7. The linear phase coefficient γ has a non-zero negative value in linear phase lens 5C1. Accordingly, micro-aperture 5C redirects scattered radiation to the left side of its optical axis so as to direct radiation from defect 3C towards imaging optic 7. In some embodiments, micro-optic layer 4, comprises an array of convex lenses and an array of prisms so that the optical axes of said convex lenses are incident on imaging optic 7. This is possible by designing the phase gradient of linear phase prisms so that the optical axes of all convex lenses in the convex lens array intersect with the optical axis of the imaging optic 7. In some embodiments, micro-optic layer 4 comprises an array of lenticular prisms whose optical axes are incident on said imaging optic. A lenticular prism refers to the combination of a convex lens with a prism. In some embodiments, the prism is implemented as a linear phase element. In some embodiments, linear phase elements are implemented separately as a linear phase micro-optic layer. In some embodiments, quadratic phase elements are implemented separately as a quadratic phase micro-optic layer. In some embodiments, quadratic phase micro-optic layer and linear phase micro-optic layer are combined as a unified micro-optic layer.

The micro-apertures of micro-optic layer 4 may be implemented using diffractive optics. Diffractive Fresnel implementations, called linear phase Fresnel lenses, of micro-apertures 5A, 5B, and 5C are shown in 5A2, 5B2, and 5C2, respectively. The linear phase Fresnel lenses were designed by computing a modulus 2π of their respective refractive optical implementations. Although the shape of refractive and diffractive optical implementations are different, their purpose is identical. Similar to their refractive optical counterparts, the diffractive optical elements also serve to collimate and redirect scattered radiation from defects. The diffractive optical elements may be implemented to either have a continuous variation in phase or a step variation in phase. The step implementation may comprise binary or multi-step implementation. For example, four step diffractive optical implementations, called linear phase quantized Fresnel lenses, of micro-apertures 5A, 5B, and 5C are shown in 5A3, 5B3, and 5C3, respectively. The step implementations may be fabricated using standard lithography. The continuous phase diffractive optical implementation may be fabricated using grayscale lithography. The refractive optical implementation may be fabricated using diamond turning. Refractive and diffractive micro-aperture maybe mass produced by first fabricating a master using diamond-turning or lithography, and by using molding to rapidly generate micro-aperture replicas. Micro-apertures may also be implemented as gradient index elements. The gradient index implementations, called linear phase gradient index lenses, of micro-apertures 5A, 5B, and 5C are shown in 5A4, 5B4, and 5C4, respectively. In a gradient index implementation, a gradient in phase is achieved by changing the refractive index of a material rather than changing its shape (as in the case of refractive and diffractive implementations). Consequently, gradient index implementations of micro-apertures look flat. A change in refractive index within a material may be accomplished by techniques such as ion implantation. Despite its different shape and material inhomogeneity, the gradient index implementation of micro-apertures serve the same purpose as refractive and diffractive optical implementations. Similar to refractive and diffractive optical implementations, the linear phase gradient index lenses serve to collimate and redirect scattered radiation from defects. Gradient index implementations may be designed by varying the refractive index of a flat substrate according to LPL(x,y).

FIG. 4A illustrates a y-z cross-section showing the use of a gas vent for holding surface 1 flat, in accordance with the invention. Surface 1 is held in place by a chuck 10A, which makes contact with surface 1 only at the edges of surface 1. This setup is particularly useful to avoid contamination to the backside of surface 1. In some embodiments, the thickness of surface 1 is not large enough to avoid gravitational sag when surface 1 is held at its edges. Accordingly, surface 1 deforms from its ideal flat shape and exhibits a concave or convex sag. In order to correct for this sag, gas is flowed through vents 11A, 11B, and 11C to create a force to compensate for gravity. In some embodiments, the direction of gas flow is towards the backside of surface 1. In other embodiments, the direction of gas flow is away from the backside of surface 1. Once the surface is made flat, a flat micro-optic layer 4 may be used effectively to collimate and redirect scattered radiation from surface 1.

FIG. 4B illustrates a cross-section showing the use of a supporting structure that makes minimal contact with the backside of surface to hold surface 1 flat, in accordance with the invention. Surface 1 is held in place by a chuck 10B which makes contact with surface 1 only at the edges of surface 1. This setup is useful to avoid any contamination to the backside of surface 1. In some embodiments, the thickness of surface 1 is not large enough to avoid gravitational sag when surface 1 is held at its edges. Accordingly, surface 1 deforms from its ideal flat shape and exhibits a concave or convex sag. In order to correct for this sag, supporting structures, 12A, 12B, and 12C, are used hold the surface flat by making minimal contact at a finite number of points on the back side of surface 1. Once the surface is made flat, a flat micro-optic layer 4 may be used effectively to collimate and redirect scattered radiation from surface 1.

In some embodiments, the sag of surface 1 is not compensated with gas vents or supporting structures. Instead, micro-optic layer 4 is designed to exhibit a similar sag as surface 1 to effectively capture scattered radiation from surface 1. In other embodiments, the focal length of different micro-apertures may be designed appropriately to compensate for sag of surface 1. For example, the focal length may be increased in regions of surface having a large sag, and the focal length may be decreased in surface regions having a small sag.

FIG. 4C illustrates a cross-section showing the illumination of a flat surface 1, in accordance with the invention. Surface 1 is held in place by a chuck 13 which holds surface 1 using vacuum suction on the back side of surface 1. Consequently, surface 1 is held flat. Therefore, a flat micro-optic layer 4 may be used effectively to collimate and redirect scattered radiation from surface 1.

FIG. 5A depicts a cross-section of a lenticular wafer inspection system with an imaging optic 7 focusing an image of micro-optic layer 4 on image sensor 8, in accordance with the invention. A defect 3B on surface 1 generates scattered radiation that is incident on a micro-aperture 5B in micro-optic layer 4. The divergence of scattered radiation is reduced by micro-optic layer 4. The micro-optic layer 4 also serves to redirect scattered radiation towards imaging optic 7. The imaging optic 7 focuses scattered radiation on image sensor 8. The focus of imaging optic 7 may be adjusted. In some embodiments, the focus of imaging optic 7 is set so as to generate an image of micro-optic layer on image sensor 8. Accordingly, image sensor 8 detects individual micro-apertures. The individual micro-apertures span over multiple pixels on image sensor 8. By analyzing the structure of pixel intensity distribution of a micro-aperture, the properties of a defect can be estimated. The scattering intensity distribution of a defect is dependent on its shape. Pixel intensities in a micro-aperture pixel region correspond to scattering intensity distribution of a defect located under the micro-aperture.

FIG. 5B depicts a cross-section of a lenticular wafer inspection system with an imaging optic 7 focusing an image of surface 1 on image sensor 8, in accordance with the invention. A defect 3B on surface 1 generates scattered radiation that is incident on a micro-aperture 5B in micro-optic layer 4. The divergence of scattered radiation is reduced by micro-optic layer 4. The micro-optic layer 4 also serves to redirect scattered radiation towards imaging optic 7. The imaging optic 7 focuses scattered radiation on image sensor 8. The focus of imaging optic 7 may be adjusted. In some embodiments, the focus of imaging optic 7 is set so as to generate an image of surface 1 on image sensor 8. In this case, image sensor 8 detects individual defects 3B. By analyzing the pixel intensity distribution of an image detected by image sensor 8, the properties of defects can be estimated. For example, the position of a defect can be estimated precisely by estimating the center of the pixel intensity distribution by fitting the measured distribution to a model of pixel intensity distribution. The size of the defect may also be predicted from the intensity of pixel values by using a calibration plot between pixel intensity and defect size.

FIG. 5C depicts a cross-section of a lenticular wafer inspection system with an image sensor 8 comprising a micro-optic sensor layer 14, in accordance with the invention. The micro-optic sensor layer 14 is different from the micro-optic layer 4. The micro-optic layer 4 reduces the divergence and redirects scattered radiation from surface 1 so that the radiation is incident on imaging optic 7. The imaging optic 7 focuses scattered radiation on the micro-optic sensor layer 14. The purpose of the micro-optic sensor layer 14 is to aid in detecting the phase of scattered radiation. After passing through the micro-optic sensor layer 14, the scattered radiation is detected by an image sensor 8.

The micro-optic sensor layer 14 comprises a plurality of lenses implemented as a refractive optical element or a diffractive optical element. In some embodiments, each lens of the micro-optic sensor layer generates an image of the aperture of the imaging optic 7 on the pixels of image sensor 8. A finite number of pixels are allocated in image sensor 8 for each lens on the micro-optic sensor layer 14. The pixels allocated for a lens of micro-optic sensor layer 14 are centered on the optical axis of the lens. From the intensities of pixels allocated for the lens, the phase gradient of scattered radiation incident on the lens is determined. For example, if the pixel intensity corresponds to a focused spot in the center of the allocated pixels (on the optical axis of lens), then the scattered radiation can be estimated to have a zero phase gradient when it is incident on the surface of the lens. Alternatively, if the pixel intensity corresponds to a focused spot that is not at the center of the allocated pixels for the lens, then the scattered light can be estimated to have a linear phase gradient that is proportional to the distance between the focused spot and the center of allocated pixels. Accordingly, a phase gradient value can be estimated for each lens of the micro-optic sensor layer 14. A phase gradient profile for the surface of the micro-optic sensor layer 14 can be estimated by combining phase gradients of a plurality of lenses in the micro-optic sensor layer 14 using a stitching algorithm. The phase profile of scattered radiation, $P(x,y)$, is computed from the estimated phase gradient profile by calculating a two dimensional integration of the phase gradient profile. The intensity of scattered light, $I(x,y)$, is obtained from the pixel intensities detected by image sensor 8. The electromagnetic field of scattered light, $C(x,y)$, is calculated from the intensity and phase of scattered radiation as, $C(x,y)=\sqrt{I(x,y)}e^{(-iP(x,y))}$. The electromagnetic field $C(x,y)$ may then be propagated using computational propagation to bring different planes in focus. For example, $C(x,y)$ may be computationally propagated to bring the micro-optic layer 4 in focus. Alternatively, $C(x,y)$ may be propagated to bring the surface 1 in focus. In some embodiments, computational propagation is performed in the spatial frequency domain by first computing spatial frequencies of electromagnetic field using a transformation. Then, a propagation transfer function is computed and multiplied with spatial frequencies of the electromagnetic field. In some embodiments, computing spatial frequencies of an electromagnetic field involves the calculation of $\tilde{C}(k_x,k_y)=F\{C(x,y)\}$, where $C(x,y)$ is electromagnetic field, F refers to Fourier transform, and $\tilde{C}(k_x,k_y)$ is the spatial frequency of $C(x,y)$. Propagation transfer function, $\tilde{H}(k_x,k_y)$, is computed as $$\tilde{H}(k_x, k_y) = e^{\left(i\Delta z \sqrt{(k^2-k_x^2-k_y^2)}\right)},$$

where $k=2\pi n/\lambda$, n is refractive index, $\lambda$ is the wavelength of the electromagnetic beam, and $\Delta z$ is the distance through which the electromagnetic field is propagated. The electromagnetic field after propagation is computed as, $F^{-1}\{\tilde{C}(k_x,$ $k_y)\tilde{H}(k_x,k_y)\}$, where $F^{-1}$ refers to inverse Fourier transformation. In other embodiments, computational propagation of an electromagnetic field is performed by first computing an impulse response or point spread function of propagation, and then computing a convolution of the electromagnetic field with the impulse response. The impulse response of propagation is calculated as $$F^{-1}\left\{e^{\left(i\Delta z\sqrt{(k^2-k_x^2-k_y^2)}\right)}\right\}.$$

In some embodiments, $\Delta z$ is calculated as the product of the square of the magnification of imaging optic 7 with the distance in z through which the field needs to be propagated in the object space (near surface 1 and micro-optic wafer 4). In some embodiments, computational propagation may be achieved by using digital refocusing algorithms that operate in the geometrical optics regime by rearranging pixel values to compute different focal planes.

Figure 6:
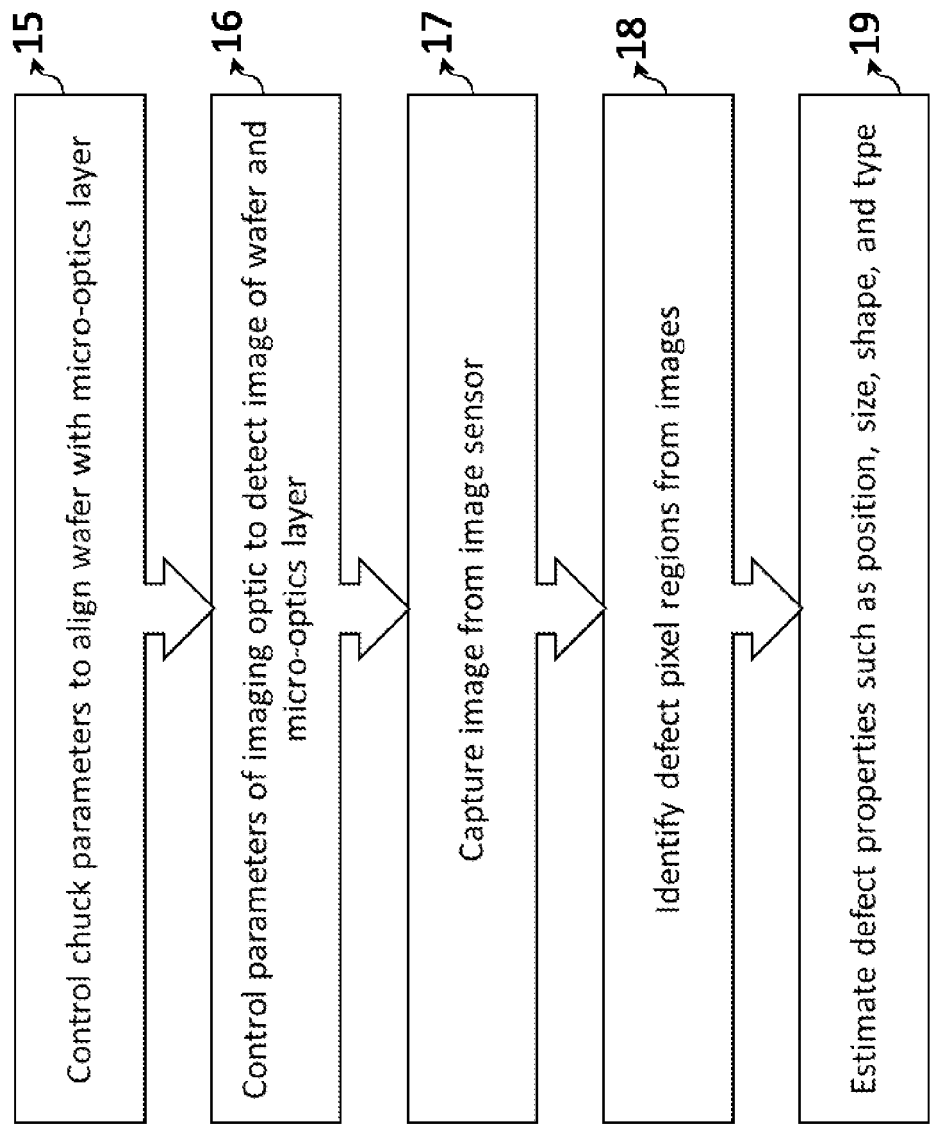
FIG. 6 shows an exemplary flow chart describing steps for estimating properties of defects on a surface, in accordance with the invention.

FIG. 6 shows an exemplary flow chart describing steps for estimating properties of defects on a surface, in accordance with the invention. In block 15, chuck parameters are adjusted to align a surface with a micro-optic layer. Adjustments performed may include tuning gas flow through vents, tuning position of supporting structures, and scanning transverse (x,y) coordinates of chuck. In some embodiments, the flow rate of gas in different gas vents may be calibrated to compensate for different wafer sags. For example, the flow rate values may be independently calibrated to achieve a uniform flatness for a given surface type, and the calibrated values may be used at a later time to achieve a desirable sag. The flatness of a wafer may be measured using a variety of techniques including interferometry, laser scanning, and structured illumination. In other embodiments, the position of different support structures may be calibrated to compensate for different wafer sags. For example, the position values for different support structures in a chuck may be independently calibrated to achieve a uniform flatness for a given surface type, and the calibrated values may be used at a later time to achieve a desirable sag. In some embodiments, surface is scanned to inspect the entire region of interest of surface. Accordingly, the position of chuck is moved so as to place the surface in a desired transverse position. In block 16, the parameters of an imaging optic are tuned to generate an image of scattered radiation on an image sensor. In some embodiments, the field of view of imaging optic is adjusted to generate an image of entire surface or an image of entire micro-optic layer on the image sensor. The field of view of imaging optic may be tuned by adjusting the zoom control of the imaging optic. In some embodiments, the focus control of the imaging optic is adjusted to generate an image of micro-optic layer on the image sensor. In other embodiments, the focus control of the imaging optic is adjusted to generate an image of surface on the image sensor. The aperture of imaging optic to may be adjusted to achieve a desirable depth of field and to reduce aberrations. In some embodiments, the aperture may be fully open to collect maximum amount of light. In other embodiments, the aperture may be tuned to have a depth of field so that either the micro-optic layer or the surface is in focus. In other embodiments, the aperture is tuned so that both micro-optic layer and surface are in focus. In block 17, an image is captured from the image sensor. Imaging parameters such as exposure time and gain are tuned to maximize image quality before capturing the image. In some embodiments, the image is captured with a micro-optic sensor layer to facilitate phase detection. In other embodiments, image is captured without a micro-optic sensor layer. In some embodiments, at least two images are captured with at least two different optical path lengths between imaging optic and image sensor. Phase is then estimated by using the transport of intensity equation. In some embodiments, optical path length between imaging optic and image sensor may be varied by using a liquid crystal layer. In other embodiments, optical path length between image sensor and imaging optic may be varied by inserting a uniform phase plate, such as a glass plate, between imaging optic and image sensor. In some embodiments, optical path length between the image sensor and the imaging optic may be varied by changing the distance between imaging optic and image sensor using an actuator. In some embodiments, an iterative optimization algorithm may be used to estimate phase profile by starting with a random initial estimate for phase and arriving at a final estimate by propagating the electromagnetic field between two or more image planes separated by the optical path length.

In some embodiments, a plurality of images obtained at different surface locations may be combined to form an image of surface. In some embodiments, a surface may be translated in transverse x and y dimensions relative to micro-optic layer so all points of interest on surface pass through the optical axis of a micro-aperture when the surface is translated. Translation of a surface may be achieved by holding the surface in place with a chuck, and translating the chuck.

In block 18, one or more images of surface is processed to separate defect pixels from background pixels. In some embodiments, a focused image of surface is used for detecting defect pixels. This is because of the presence of high intensity values of defect pixels in focused images. In a focused image of a surface, defect pixels may be classified from their background pixels using an intensity threshold value. To minimize false positives, threshold values are designed to be higher than background pixel values. The value of a threshold may be adaptively chosen depending on pixel intensities in local neighborhood. For example, threshold value in a region with high background is higher than the threshold value in a region with lower background. In some embodiments, a focused defect may be modeled and the model shape may be correlated with image of surface. Such a correlation operation creates correlation peaks at the position of defects. Correlation peaks may then be distinguished from their background using an intensity threshold value. For each defect, a defect pixel region, comprising a predetermined number of pixels that are surrounding the detected defect pixels, is segmented for estimating defect properties.

In block 19, a defect pixel region is processed to estimate defect properties such as position on wafer, size, shape, and type. Multiple images of surface, including focused and defocused images, may be used for estimating defect properties. An image of micro-optic layer may also be used for estimating defect properties. The position of a defect on a surface may be accurately estimated by comparing a model of defect with the defect pixel region. For example, error values between model and measured defect pixels is computed for a variety of position values. The position value with least error is estimated as the position of defect on surface. In some embodiments, the position of a defect may also be estimated from peak, centroid, or midpoint of the defect pixel region. The size of defect may be calculated by measuring the width of the defect along one, two, or three dimensions from multiple focused and defocused images of surface. Size of defect may refer to length, area, or volume of a defect. The shape of a defect may be obtained from defect pixel regions in multiple focused and defocused images. The shape of defect may also be obtained from an image of micro-optic layer. In some embodiments, a defocused image of a surface or an image of micro-optic layer may comprise more information about the shape of defect than a focused image. This is because scattered radiation from defect is detected by more number of pixels in a defocused image or in an image of micro-optic layer than in a focused image. The defect pixels may be fitted with models of focused and defocused defect profiles. Comparisons may include comparisons of both pixel intensity and pixel phase. Models of defects include scaled, rotated, translated, and other deformed versions of numerous known defect types such as particles, process induced defects, ellipsoids, crystal originated pits (COP), bumps, scratches, and residues. In some embodiments, an error metric is computed by calculating the difference between defect pixels and model pixels. The model with minimum error value may be declared as an estimate of defect type.

Figure 7:
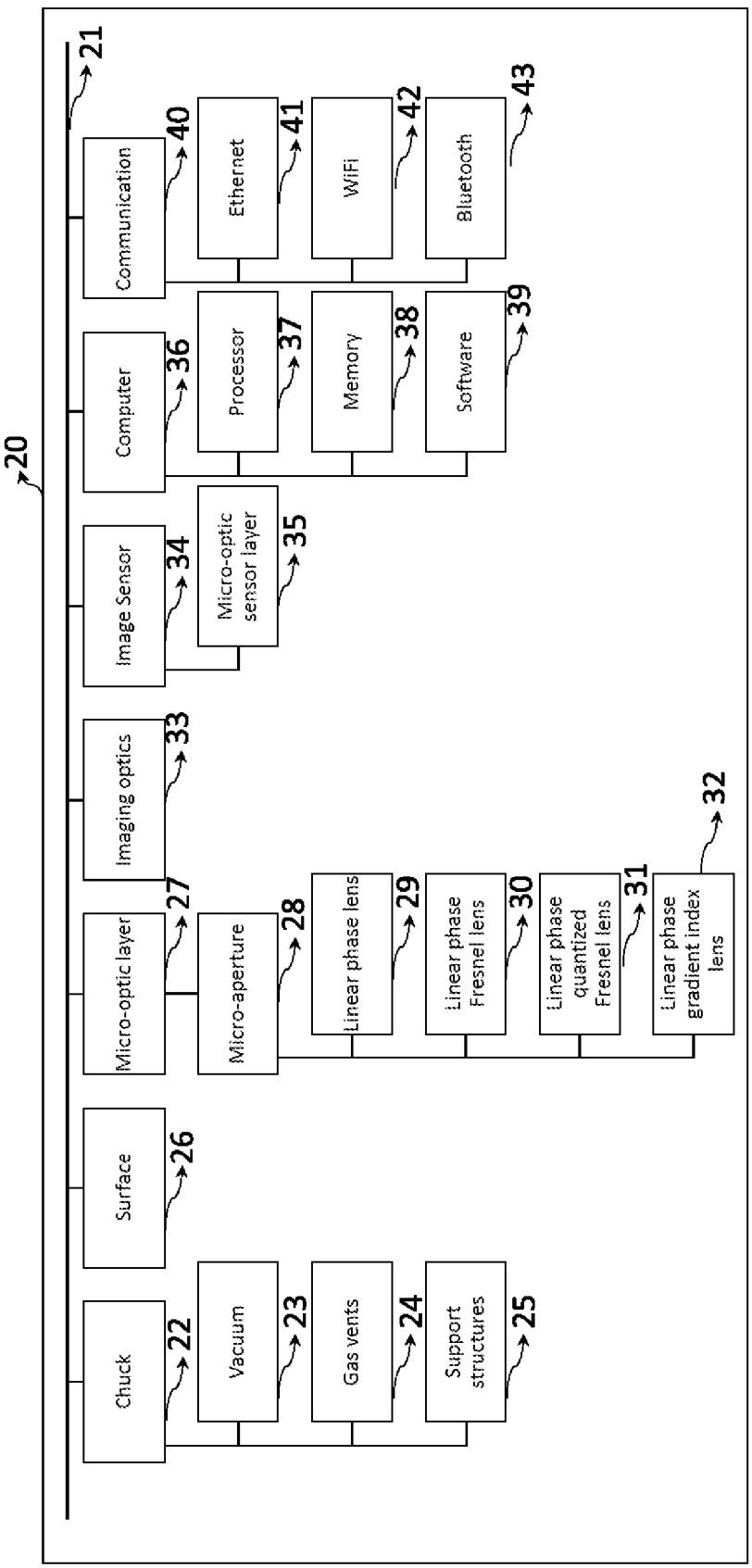
FIG. 7 illustrates a block diagram of a system for lenticular wafer inspection, in accordance with the invention.

FIG. 7 illustrates a block diagram of a system for lenticular wafer inspection 20, in accordance with the invention. A bus 21 connects various blocks of system 20, namely chuck 22, surface 26, illumination, micro-optic layer 27, imaging optic 33, image sensor 34, computer 36, and communication 40. Data and control signals are carried by bus 21. Chuck 22 includes an edge handling system that holds the edge of surface, vacuum system 23 that holds the back side of surface with vacuum suction, gas vents 24, and support structures 25 used to hold surface 26 flat. Surface 26 comprises the region to be illuminated by system 20. Surface 26 may be flat, curved due to gravity induced sag, or deformed due to coatings. Illumination includes laser beams and beam expanders. Micro-optic layer comprises a plurality of micro-apertures 28. Micro-aperture 28 includes a linear phase lens 29, linear phase Fresnel lens 30, linear phase quantized Fresnel lens 31, and linear phase gradient index lens 32. Image sensor 34 captures scattered radiation from surface and transfers image data through bus 21 to computer 36. In some embodiments, Image sensor 34 includes a micro-optic sensor layer 35. Image sensor 34 receives control information to adjust parameters such as exposure time and gain from computer through bus 21. Computer 34 includes a processor 37, memory 38, and software 39. Software 39 processes image data from image sensor to compute a number of entities, including: intensity and phase profiles of electromagnetic field; computational propagation to compute image of scattered radiation; image of surface or image of micro-optic layer by combining a plurality of images of scattered radiation; defect pixel region; defect properties such as position, size, shape, and type. Software 39 generates control information and sends them through bus 21 to chuck 22, surface 26, illumination, image sensor 34, and micro-optic layer 27. Computer 36 connects to communication block 40 for communicating data and control information through bus 21. Communication block 40 includes Ethernet 41, WiFi 42, and Bluetooth 44.

It will be recognized by those skilled in the art that various modifications may be made to the illustrated and other embodiments of the invention described above, without departing from the broad inventive scope thereof. It will be understood therefore that the invention is not limited to the particular embodiments or arrangements disclosed, but is rather intended to cover any changes, adaptations or modifications which are within the scope and spirit of the invention as defined by the appended claims.

It should be understood that the present invention as described above can be implemented in the form of control logic using computer software in a modular or integrated manner. Based on the disclosure and teachings provided herein, a person of ordinary skill in the art will know and appreciate other ways and/or methods to implement the present invention using hardware and a combination of hardware and software.

Any of the software components or functions described above, may be implemented as software code to be executed by a processor using any suitable computer language such as, for example, Java, C++ or Perl using, for example, conventional or object-oriented techniques. The software code may be stored as a series of instructions, or commands on a computer readable medium, such as a random access memory (RAM), a read only memory (ROM), a magnetic medium such as a hard-drive or a floppy disk, or an optical medium such as a CD-ROM. Any such computer readable medium may reside on or within a single computational apparatus, and may be present on or within different computational apparatuses within a system or network.

In the claims, reference to an element in the singular is not intended to mean "one and only one" unless explicitly stated, but rather is meant to mean "one or more." In addition, it is not necessary for a device or method to address every problem that is solvable by different embodiments of the invention in order to be encompassed by the claims.

The above description is illustrative and is not restrictive. Many variations of the disclosure will become apparent to those skilled in the art upon review of the disclosure. The scope of the disclosure should, therefore, be determined not with reference to the above description, but instead should be determined with reference to the pending claims along with their full scope or equivalents.

One or more features from any embodiment may be combined with one or more features of any other embodiment without departing from the scope of the disclosure. Further, modifications, additions, or omissions may be made to any embodiment without departing from the scope of the disclosure. The components of any embodiment may be integrated or separated according to particular needs without departing from the scope of the disclosure.

What is claimed is:

1. A system for inspecting a surface, comprising:
   an electromagnetic radiation incident on said surface to generate scattered radiation from features of said surface;
   a quadratic phase micro-optic layer disposed to reduce the divergence of said scattered radiation by inducing a plurality of substantially quadratic phase shifts;
   a linear phase micro-optic layer disposed to redirect said scattered radiation towards a predetermined spatial region by inducing a plurality of substantially linear phase shifts;
   an imaging optic located in said spatial region to focus said radiation from said micro-optic layer; and
   an image sensor positioned to detect radiation from said imaging optic to generate an image of radiation,
   whereby said features of said surface are detected in said image of radiation.

2. The system of claim 1, wherein said quadratic phase micro-optic layer comprises an array of convex lenses.

3. The system of claim 2, wherein said lenses have a focal length substantially equal to the distance between said surface and said quadratic phase micro-optic layer.

4. The system of claim 1, wherein said linear phase micro-optic layer comprises an array of prisms.

5. The system of claim 1, wherein said linear phase micro-optic layer comprises an array of linear phase elements, with each element having: a phase gradient proportional to the distance between said element and the point of intersection of the optical axis of said imaging optic with said linear phase micro-optic layer; and an azimuthal direction substantially equal to the direction of said point of intersection from said element.

6. The system of claim 1, wherein said quadratic phase micro-optic layer and said linear phase micro-optic layer are combined as a unified micro-optic layer.

7. The system of claim 6, wherein said unified micro-optic layer comprises an array of lenticular prisms.

8. The system of claim 1, wherein at least one micro-optic layer comprises refractive optical elements.

9. The system of claim 1, wherein at least one micro-optic layer comprises diffractive optical elements.

10. The system of claim 1, wherein said imaging optic is focused so that an image of at least one micro-optic layer is detected by said image sensor.

11. The system of claim 1, wherein said imaging optic is focused so that an image of said surface is detected by said image sensor.

12. The system of claim 1, wherein said image sensor comprises a micro-optic sensor layer to detect phase of said radiation.

13. The system of claim 1, wherein said surface is held flat by using a gas vent or a supporting structure.

14. The system of claim 1, further comprising means for varying optical path length between said imaging optic and said image sensor so that said radiation is detected at multiple values of optical path length.

15. The system of claim 1, further comprising means for scanning said surface relative to at least one micro-optic layer so that radiation from a plurality of regions on said surface are detected when said surface is scanned.

16. The system of claim 1, wherein said electromagnetic radiation has a wavelength that maximizes reflected power from said surface.

17. The system of claim 1, wherein said electromagnetic radiation has a polarization that maximizes reflected power from said surface.

18. The system of claim 1, wherein said electromagnetic radiation has a wavelength that maximizes quantum efficiency of said image sensor.

19. A method for inspecting a surface, comprising:

illuminating said surface with an electromagnetic radiation to generate scattered radiation from features of said surface;

reducing the divergence of said scattered radiation by inducing a plurality of substantially quadratic phase shifts;

redirecting said scattered radiation towards a predetermined spatial region by inducing a plurality of substantially linear phase shifts;

focusing after said radiation has propagated to said spatial region;

capturing an image of radiation, whereby said features of said surface are detected in said image of radiation.

20. The method of claim 19, further comprising detection of defect pixels from said image of radiation and estimation of defect properties from said defect pixels.

* * * * *